United States Patent [19]
Loomans et al.

[11] Patent Number: 4,847,303
[45] Date of Patent: * Jul. 11, 1989

[54] TERT-BUTYLPHENYL COMPOUNDS USEFUL AS ANTI-INFLAMMATORY AGENTS

[75] Inventors: Maurice E. Loomans; Randall S. Matthews, both of Cincinnati, Ohio; Joseph A. Miller, Baton Rouge, La.

[73] Assignee: The Procter & Gamble Company, Cincinnati, Ohio

[ * ] Notice: The portion of the term of this patent subsequent to Nov. 24, 2004 has been disclaimed.

[21] Appl. No.: 123,694

[22] Filed: Nov. 23, 1987

[51] Int. Cl.$^4$ ............................................. A61K 31/12
[52] U.S. Cl. .................... 514/689; 568/662; 568/663; 568/627; 564/366; 564/342; 564/372; 564/374; 564/285; 564/223; 564/169; 260/410.5; 562/463
[58] Field of Search ................ 560/142, 130; 558/415, 558/416, 427, 436, 441; 568/775, 784, 308, 337, 662, 663, 627; 564/366, 342, 372, 374, 285, 223, 169; 260/410.5; 562/463; 514/689, 545, 546, 733, 678, 649, 643, 629, 621, 570

[56] References Cited

U.S. PATENT DOCUMENTS

| | | | |
|---|---|---|---|
| 3,717,611 | 2/1973 | Baumer et al. | 260/45.95 G |
| 4,130,666 | 12/1978 | Moore | 424/331 |
| 4,431,656 | 2/1984 | Katsumi et al. | 424/273 R |
| 4,440,784 | 4/1984 | Katsumi et al. | 424/308 |
| 4,708,966 | 11/1984 | Loomans et al. | 514/689 |
| 4,711,903 | 12/1987 | Deason et al. | 514/381 |

FOREIGN PATENT DOCUMENTS

| | | | |
|---|---|---|---|
| 60-54315 | 3/1985 | Japan | 424/308 |
| 61-218571 | 3/1985 | Japan | 424/308 |

OTHER PUBLICATIONS

Hauff, Krauss & Rieker, "Spin Density Distribution in Free Radicals, VII, Participation of the Carbon-Carbon Bond in the Mesomerism of Phenoxy Radicals", *Chem. Ber.*, vol. 105, No. 4 (172), pp. 1446-1455.

Gavrilov, Meshcheryakov, Kalyagina, Dobronravova & Vereshchagin, "Synthesis of Diarylpropynones and Their Antibiotic Activity", *Khimiko-Farmatsevticheskii Zhurnal*, vol. 12, No. 9 (Sept. 1978), pp. 42-56.

Swingle, Bell & Moore, "Anti-Inflammatory Activity of Antioxidants", Chapter 4 of Anti-Inflammatory and Anti-Rheumatic Drugs, vol. III, Rainsford (ed.), CRC Press, Inc., Boca Raton, Fla., 1985, pp. 105-126.

*Soviet Inventions Illustrated*, Week 8429, SU 1054-34-2-A, Derwent Publications, Ltd., London, England.

Magnusson, "Reactions Between Quinones and Carbonyl Compounds Catalyzed by Aluminium Oxide", *Acta Chemica Scandinavica*, vol. 18, No. 2 (164), pp. 421-432.

*Primary Examiner*—James H. Reamer
*Attorney, Agent, or Firm*—Milton B. Graff, IV; Jack D. Schaeffer; Richard C. Witte

[57] ABSTRACT

The present invention involves compounds having the structure:

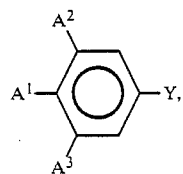

wherein:
(a) —$A^1$ is selected from the group consisting of —OH, —H, and —$O_2CR$;
(b) —$A^2$ is selected from the group consisting of unsubstituted or substituted, saturated or unsaturated, straight, branched and cyclic alkyl having from 1 to about 10 carbon atoms;
(c)—$A^3$ is selected from —$C(CH_3)_3$, —$Si(CH_3)_3$, and —$CF_3$; and
(d) —Y is selected from certain low molecular weight alkyl chains which terminate in specific unsaturated functional groups:

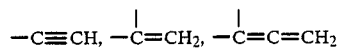

and aldehydes in the form of their acetals; pharmaceutical compositions comprising such compounds; and methods for treating inflammation by administering such compounds.

25 Claims, No Drawings

TERT-BUTYLPHENYL COMPOUNDS USEFUL AS ANTI-INFLAMMATORY AGENTS

BACKGROUND OF THE INVENTION

The present invention relates to novel specifically-substituted phenyl compounds, especially substituted tert-butylphenol compounds, which are effective as anti-inflammatory, analgesic and/or antipyretic agents. The present invention further relates to pharmaceutical compositions which are useful for treating diseases which involve inflammation, pain, and/or fever. Finally, the present invention relates to methods for treating diseases characterized by inflammation.

The search for new non-steroidal anti-inflammatory ("NSAI") drugs over the last 10 to 20 years has led to the testing by various researchers and companies of thousands of compounds for efficacy as anti-inflammatories. The search has raised many questions, but provided few answers, about how and why some compounds are efficacious and others are not, especially for substituted tert-butylphenol compounds. This search, and the results and questions raised thereby, are discussed more fully in "Anti-inflammatory Activity of Anti-oxidants", by K. F. Swingle, et al., Chapter 4 of *Anti-inflammatory and Anti-rheumatic Drugs*, Vol. III (K. D. Rainsford, Editor; CRC Press, Inc.; 1985), pages 105-126, which is incorporated herein by reference.

Notwithstanding the great effort already put forth to identify NSAI drugs, there remains a continuing need to identify new compounds and compositions which are effective for treating inflammation and inflammatory diseases such as rheumatoid arthritis and osteoarthritis. It is accordingly an object of the present invention to provide compounds which are effective anti-inflammatory agents, as well as pharmaceutical compositions containing these compounds. It is a further object of the present invention to provide methods for treating diseases characterized by inflammation.

It is a further object of the present invention to provide compounds which have one or more of the following uses: anti-inflammatory agents, analgesic agents, antipyretic agents, antioxidant agents, antiarthritic agents, bone modifying agents, immunomodulating agents, antilipidemic agents, antiresorptive agents or agents for reversing ischaemia-induced cell damage; and pharmaceutical compositions containing these compounds. A still further object of the present invention is to provide compounds, and compositions containing these compounds, which have high efficacy, low toxicity (such as low gastrointestinal irritability), prolonged duration of action, and/or good therapeutic indices.

These and other objects wil become readily apparent from the detailed description which follows.

SUMMARY OF THE INVENTION

The present invention relates to specifically-substituted phenyl compounds, preferably substituted 6-tert-butylphenol compounds, which are effective as one or more of the following: anti-inflammatory agents, analgesic agents, antipyretic agents, antioxidant agents, antiarthritic agents, immunomodulating agents, antilipidemic agents, antiresorptive agents or agents for reversing ischaemia-induced cell damage. These phenyl compounds are substituted in the 4-position with a low molecular weight alkyl chain which terminates in a specific unsaturated functional group. These unsaturated functionalities are

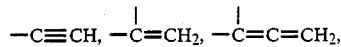

and aldehydes in the form of their acetals.

The present invention further relates to pharmaceutical compositions. These compositions comprise a compound of the present invention and a pharmaceutically-acceptable carrier.

Finally, the present invention also relates to methods for treating diseases characterized by inflammation, such as rheumatoid arthritis and osteoarthritis, in humans or lower animals. Such methods comprise administering to a human or lower animal in need of such treatment a safe and effective amount of a compound or composition of the present invention.

DETAILED DESCRIPTION OF THE INVENTION

Anti-inflammatory Agents

The compounds useful in the present invention are specifically-substituted phenyl compounds. Preferably, the compounds of the present invention are phenol compounds substituted in the 6-position with a t-butyl, trimethylsilyl or trifluoromethyl group; substituted in the 2-position with a low molecular weight, unsubstituted or substituted, saturated or unsaturated, branched, straight or cyclic alkyl group; and substituted in the 4-position with a specific low-molecular-weight alkyl chain which terminates in a specific unsaturated functional group. The terminal functionality of the 4-position substituent is selected from

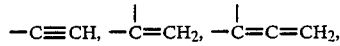

or aldehydes in the form of their acetals. Preferred are the —C≡CH and acetal terminal functionalities.

Specifically, the compounds of the present invention have the general structure:

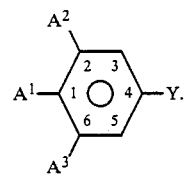

In this structure, —$A^1$ is selected from the group consisting of —OH, —H, and —$O_2CR$; and wherein —R is a straight or branched chain alkyl group having from 1 to about 10 carbon atoms, preferably methyl or ethyl. Preferred —$A^1$ is —OH or —H, and most preferred —$A^1$ is —OH.

—$A^2$ is selected from the group consisting of unsubstituted or substituted, saturated or unsaturated, straight, branched or cyclic alkyl having from 1 to about 10 carbon atoms; except for $C_4$ to $C_{10}$ straight-chain, saturated alkyl and tert-butyl. Substituents of —$A^2$ may be one or more of the group consisting of halo, —$OR^3$, —$O_2CR^3$, —$CO_2R^3$, and —$C(O)R^3$. Preferred is unsubstituted —$A^2$ or —$A^2$ substituted with hydroxy or halo, especially fluoro. More preferred —$A^2$ is selected from unsubstituted $C_1$-$C_3$ saturated straight-chain alkyl, $C_2$-$C_6$ unsaturated straight-chain alkyl, and $C_3$-$C_6$ saturated or unsaturated branched-chain alkyl. Preferred unsaturated —$A^2$'s have a terminally unsaturated group.

—$A^3$ is selected from the group consisting of t-butyl, trimethylsilyl or trifluoromethyl. Preferred —$A^3$ is t-butyl.

—Y is a terminally unsaturated group selected from the group consisting of:

1. —$(CR^1{}_2)_n$—C≡C—H, wherein n is an integer from 1 to about 6;
2. 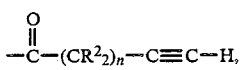

wherein n is an integer from 0 to about 5;
3. 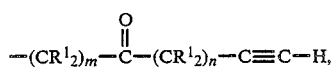

wherein m is an integer from 1 to about 5, and m+n is an integer from 1 to about 5; preferred is m=2;
4. 

wherein n is 0 or 1;
5. —$(CR^1{}_2)_n$—$CR^3$=$CH_2$, wherein n is an integer from about 2 to about 6;
6. 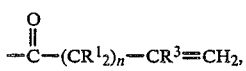

wherein n is an integer from 0 to about 5;
7. 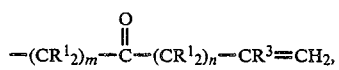

wherein m is an integer from 1 to about 3, and m+n is an integer from 1 to about 3; preferred is m=2;
8. 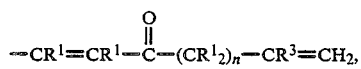

wherein n is an integer from 0 to about 3;
9. —$(CR^1{}_2)_n$—$CR^3$=C=$CH_2$, wherein n is an integer from 0 to about 6;
10. 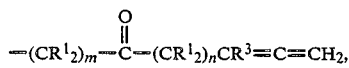

wherein m+n is an integer from 0 to about 5; preferred is m=0 or 2;
11. 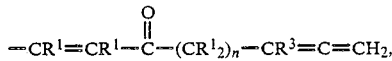

wherein n is an integer from 0 to about 3;
12. —$(CR^1{}_2)_n$—$CH(ZR^4)_2$, wherein n is an integer from 1 to about 6; and
13. 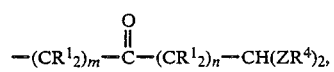

wherein n is an integer from 1 to about 5, m is an integer from 0 to about 4, and m+n is an integer from about 1 to about 5; preferred is m=0 or 2.

In these substituent —Y groups, each —$R^1$ is independently selected from the group consisting of —H, —$OR^3{}_2$, —$NR^3{}_3{}^+$, —$N(R^3)C(O)R^3$, —$O_2CR^3$, —$CO_2R^3$, —$C(O)NR^3{}_2$, straight or branched chain saturated alkyl group having from 1 to about 3 carbon atoms, and straight or branched chain unsaturated alkyl group having from 1 to about 3 carbon atoms, or two —$R^1$'s on the same carbon atom are =O or =$CR^3{}_2$. Preferably, —$R^1$ is —H, —OH, methyl, or ethyl, or two —$R^1$'s on the same carbon atom are =O or =$CH_2$, and further preferred is no more than about two —$R^1$ groups being other than —H. Most preferred is all —$R^1$ groups being —H.

Each —$R^2$ is independently selected from the group consisting of —H, —$OR^3$, —$NR^3{}_2$, —$NR^3{}_3{}^+$, —$N(R^3)C(O)R^3$, —$O_2CR^3$, —$CO_2R^3$, —$C(O)NR^3{}_2$, straight or branched chain saturated alkyl group having from 1 to about 3 carbon atoms, and straight or branched chain unsaturated alkyl group having from 1 to about 2 carbon atoms, or two —$R^2$'s on the same carbon atom are =O or =$CR^3{}_2$. Preferably, —$R^2$ is —H, —OH, methyl, or ethyl, or two —$R^2$'s on the same carbon atom are =O or =$CH_2$, and further preferred is no more than about two —$R^2$ groups being other than —H. Most preferred is all —$R^2$ groups being —H.

Each —$R^3$ is independently selected from the group consisting of —H, methyl and ethyl. Preferably —$R^3$ is —H.

Each —$R^4$ is independently selected from the group consisting of —$CH_3$ and —$CH_2CH_3$, or the —$R^4$'s may be joined to form a cyclic acetal such that both —$R^4$'s together are one group selected from —$(CH_2)_2$— and —$(CH_2)_3$—. Preferred is both —$R^4$ groups being methyl, or both —$R^4$ groups together being —$CH_2CH_2$—. Most preferred is both —$R^4$ groups being methyl.

Each —Z— is independently selected from the group consisting of —O—, —S—, —NH—, and —$NR^4$—. Preferred is —Z— being —O— or —S—, and most preferred is both —Z— groups being the same atom selected from —O— or —S—.

Specifically preferred acetal groups (i.e., —$CH(ZR^4)_2$ groups) are

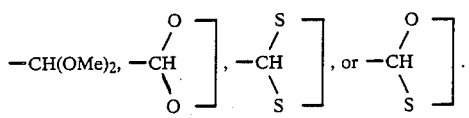

Most preferred specific acetals are

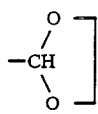

and, especially, —CH(OMe)$_2$.

Preferred —Y groups are those having terminal —C≡CH or acetal functionalities:

1. —(CR$^1_2$)$_n$—C≡CH, wherein n is an integer from 1 to about 6;
2.

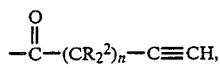

wherein n is an integer from 0 to about 5;

3.

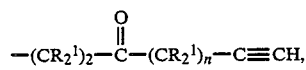

wherein n is an integer from 0 to about 3;

4.

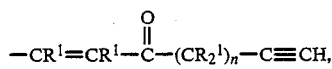

wherein n is 0 or 1;

5. —(CR$^1_2$)$_n$—CH(ZR$^4$)$_2$, wherein n is an integer from 1 to about 6;

6.

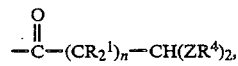

wherein n is an integer from 1 to about 5; and

7.

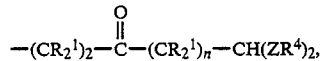

wherein n is an integer from 1 to about 3.

Most preferred —Y groups are:

1.

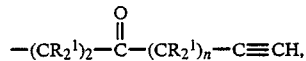

wherein n is an integer from 0 to about 3;

2.

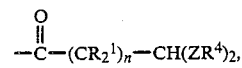

wherein n is an integer from 1 to about 5; and, especially,

3.

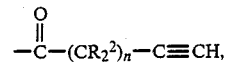

wherein n is an integer from 0 to about 5; more preferred is wherein n is an integer from 1 to about 4; most preferred is n=3.

The compounds of the present invention include their pharmaceutically-acceptable salts. The term "pharmaceutically-acceptable salts", as used herein, means the compounds in their salt form which have the same general pharmacological properties as the protonated form from which they are derived, and which are acceptable from a toxicity viewpoint. Pharmaceutically-acceptable salts include alkali metal (e.g., sodium and potassium), alkaline earth metal (e.g., calcium and magnesium), non-toxic heavy metal (e.g., stannous and indium), and ammonium and low molecular weight substituted ammonium (mono-, di- and tri-methyl or ethyl ammonium) salts. Preferred are the sodium, potassium, and ammonium salts.

The compounds of the present invention have utility as one or more of the following: anti-inflammatory agents, analgesic agents, antipyretic agents, antioxidant agents, antiarthritic agents, immunomodulating agents, antilipidemic agents, anti-resorptive agents, anti-aging agents or agents for reversing ischaemia-induced cell damage; and are potentially useful for treating one or more of the following diseases or conditions: rheumatoid arthritis, osteoarthritis, bone loss diseases, periodontal disease, gingivitis, allergic rhinitis, asthma, hay fever, shock lung and pulmonary edema, bronchitis and emphysema, signs and symptoms associated with colds and flu, Crohn's disease, inflammatory bowel disease, myocardial infarction (ischemic damage from reperfusion), post-stroke ischemic damage to brain, contact dermatitis, psoriasis, atopic dermatitis, poison ivy, urticaria, allergic eczema, allergic conjuctivitis, atherosclerosis, anaphylactic shock, cerebral stroke damage, gout, organ transplant rejection, tissue trauma and burns, inflammation reactions of the CNS (i.e., multiple sclerosis), sunburn, and high serum cholesterol. Furthermore, the phenolic compounds of the present invention may be useful as antioxidants for various non-pharmaceutical uses.

In order to determine and assess pharmacological activity, testing of these compounds in animals is carried out using various assays known to those skilled in the art. Thus, the anti-inflammatory activity of the compounds can be conveniently demonstrated using an assay designed to test the ability of these compounds to antagonize the local edema which is characteristic of the inflammatory response. Examples of such known tests include the carrageenan rat edema test, the oxazolone-induced inflamed mouse ear test, and the arachidonic acid-induced inflamed mouse ear test. Antipyretic activity may be tested using art-known rat models, and analgesic activity may be tested in art-known models such as the acetylcholine model in mice, the Randall-Selitto model in rats, and the hot-plate test in mice or rats. Another useful art-known test is the adjuvant arthritis test which is a useful model for assessing anti-inflammatory activity, antiarthritic and anti-resorptive activity in a chronic, rather than acute, model.

These and other appropriate tests for pharmacological activity are disclosed and/or referred to in U.S. Pat. No. 4,130,666, issued Dec. 19, 1978 to Moore; U.S. Pat. No. 4,440,784, issued Apr. 3, 1984 to Katsumi et al.; Japanese Patent Application No. 85/54315, published Mar. 28, 1985 by Katsumi et al.; European Patent Application Publication No. 59,090, published Sept. 1, 1982 by Yamanouchi Pharmaceutical Co., Ltd.; "Prostaglandin and Leukotriene Synthesis in Mouse Ears Inflamed by Arachidonic Acid", *The Journal of Investigative Dermatology*, 84, pp. 253–256 (1985); U.S. Pat. No. 4,431,656, issued Feb. 14, 1984, to Katsumi et al.; "Antiinflammatory Activity of Antioxidants", by K. F. Swingle, et al., Chapter 4 of *Anti-inflammatory and Antirheumatic Drugs*, Vol. III (K. D. Rainsford, Editor; CRC Press, Inc., 1985); Adamkiewicz et al., *Canad. J. Biochem. Physio.*, 33, 332 (1955); Selye, *Brit. Med. J.*, 2, 1129 (1949); and Winter, *Proc. Exper. Biol. Med.*, 111, 554 (1962); the disclosures of all these patents and articles being incorporated herein by reference.

The compounds of the present invention are prepared from commercially-available materials. Synthesis techniques disclosed for compounds related to the compounds of the present invention can be adapted by a skilled chemist for the preparation of the present compounds; such synthesis techniques are described, for example, in U.S. Pat. Nos. 4,130,666 and 4,440,784, and in Japanese Patent Application No. 85/54315, and in copending U.S. patent application Ser. No. 879,863 of Loomans, Matthews and Miller, filed June 27, 1986 (U.S. Pat. No. 4,708,966, issues Nov. 24, 1987), all of which are hereby incorporated by reference, as well as in several other of the patents and articles incorporated hereinbefore by reference. Representative procedures for synthesizing compounds of the present invention are provided in the Examples hereinafter.

The compounds of the present invention typically comprise from about 0.1% to about 99.9% by weight of the pharmaceutical compositions of the present invention, preferably from about 20% to about 80%, and most preferably from about 40% to about 80%.

As demonstrated by the animal test results provided in the Examples hereinafter, the compounds of the present invention are effective anti-inflammatory agents. Some of the compounds further surprisingly show antiinflammatory activity at very low dosage levels. In addition, some of the compounds of the present invention are expected to have surprisingly low toxicity, including very little gastrointestinal irritation even when dosed at levels well above dosage levels effective as anti-inflammatory agents. Thus, some of the compounds of the present invention would have very good therapeutic indices. Furthermore, some compounds of the present invention are expected to have prolonged duration of action. This would permit less frequent dosing for the compounds of the present invention relative to the typical dosing every 4–6 hours for most commercially-available anti-inflammatory drugs.

Pharmaceutically-acceptable Carrier

In addition to the anti-inflammatory agent as described hereinbefore, the pharmaceutical compositions of the present invention essentially contain a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the pharmaceutical composition are capable of being commingled with the anti-inflammatory agent, and with each other, in a manner such that there is no interaction which would substantially reduce the pharmaceutical efficacy of the pharmaceutical composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers are sugars such as lactose, glucose and sucrose; starches such as cornstarch and potato starch; cellulose and its derivatives such as sodium carboxymethylcellulose, ethylcellulose, cellulose acetate; powdered tragacanth; malt; gelatin; talc; stearic acid; magnesium stearate; calcium sulfate; vegetable oils such as peanut oil, cottonseed oil, sesame oil, olive oil, corn oil and oil of theobroma; polyols such as propylene glycol, glycerine, sorbitol, mannitol, and polyethylene glycol; agar; alginic acid; pyrogen-free water; isotonic saline; and phosphate buffer solutions, as well as other non-toxic compatible substances used in pharmaceutical formulations. Wetting agents and lubricants such as sodium lauryl sulfate, as well as coloring agents, flavoring agents, excipients, tableting agents, stabilizers, antioxidants, and preservatives, can also be present. Other compatible pharmaceutical additives and actives (e.g., other NSAI drugs; pain killers; muscle relaxants) may be included in the pharmaceutically-acceptable carrier for use in the compositions of the present invention.

The choice of a pharmaceutically-acceptable carrier to be used in conjunction with the anti-inflammatory agents of the present composition is basically determined by the way the compound is to be administered. If the compound is to be injected, the preferred pharmaceutically-acceptable carrier is sterile, physiological saline, with blood compatible suspending agent, the pH of which has been adjusted to about 7.4. Suitable pharmaceutically-acceptable carriers for topical application include those suited for use in creams, gels, tapes and the like.

The preferred mode of administering the compounds of the present invention is orally. The preferred unit dosage form is therefore tablets, capsules and the like, comprising a safe and effective amount of the anti-inflammatory compound of the present invention, which is preferably from about 10 mg to about 3500 mg, more preferably from about 25 mg to about 1000 mg, and most preferably from about 25 mg to about 600 mg. Pharmaceutically-acceptable carriers suitable for the preparation of unit dosage forms for oral administration are well-known in the art. Their selection will depend on secondary considerations like taste, cost, shelf stability, which are not critical for the purposes of the present invention, and can be made without difficulty by a person skilled in the art.

The pharmaceutically-acceptable carrier employed in conjunction with the anti-inflammatory agents of the present invention is used at a concentration sufficient to provide a practical size to dosage relationship. The pharmaceutically-acceptable carriers, in total, may comprise from about 0.1% to about 99.9% by weight of the pharmaceutical compositions of the present invention, preferably from about 20% to about 80%, and most preferably from about 20% to about 60%.

Method for Treating Diseases Characterized by Inflammation

Another aspect of the present invention is methods for treating diseases characterized by inflammation. Such methods comprise administering to a human or lower animal in need of such treatment of a safe and effective amount of an anti-inflammatory agent described hereinbefore.

The preferred mode of administration is oral, but other known methods of administration are contemplated as well, e.g., dermatomucosally (for example, dermally, rectally and the like) and parenterally (for example, by subcutaneous injection, intramuscular injection, intra-articular injection, intravenous injection and the like). Ocular administration and inhalation is also included. Thus, specific modes of administration include, without limitation, oral, transdermal, mucosal, sublingual, intranasal, intramuscular, intravenous, intraperitoneal, and subcutaneous administration, as well as topical application.

The term "diseases characterized by inflammation", as used herein, means conditions which are known to involve inflammation, such as arthritis (e.g., rheumatoid arthritis; osteoarthritis; psoriatic arthritis; juvenile arthritis; Reiter's syndrome; infectious arthritis; ankylosing spondylitis; systemic lupus erythematosus; and gout), as well as the presence of inflammation whether or not it is associated with an identifiable disease. Diseases characterized by inflammation further include inflammation of the gastrointestinal tract, including the oral cavity (e.g., inflammation associated with gingivitis or periodontal disease) and bowels (e.g., inflammation associated with Inflammatory Bowel Disease); inflammation associated with dermatological disease (e.g., psoriasis); and inflammation associated with the respiratory tract (e.g. pulmonary inflammation).

The phrase "safe and effective amount", as used herein, means an amount of a compound or composition high enough to significantly positively modify the condition to be treated, but low enough to avoid serious side effects (at a reasonable benefit/risk ratio), within the scope of sound medical judgment. The safe and effective amount of the anti-inflammatory agent will vary with the particular condition being treated, the age and physical condition of the patient being treated, the severity of the condition, the duration of the treatment, the nature of concurrent therapy, the specific anti-inflammatory agent employed, the particular pharmaceutically-acceptable carrier utilized, and like factors within the knowledge and expertise of the attending physician. However, single dosages can range from about 10 mg to about 3500 mg, or from about 0.2 mg/kg of body weight to about 70 mg/kg of body weight. Preferred single dosages are from about 25 mg to about 600 mg, or from about 0.5 to about 12 mg/kg of body weight. Up to about 6 single dosages per day may be administered.

The following Examples further describe and demonstrate preferred embodiments within the scope of the present invention. The Examples are given solely for the purpose of illustration, and are not to be construed as limitations of the present invention since many variations thereof are possible without departing from its spirit and scope. All temperature readings are in °C.

EXAMPLE 1

Synthesis of 2-methyl-4-(5'-hexynoyl)-6-t-butylphenol

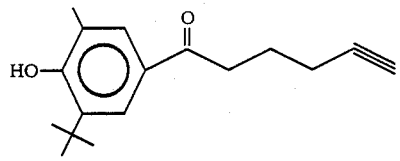

To a solution of 2-tert-butylphenol (18 ml, 117 mmol) in 117 mL methylene chloride, stirred at 0° C., is added bromine (2.1 equiv, 39 g). The reaction is allowed to reach room temperature and is stirred 15 minutes more. The product is then extracted from water using 3 100 mL portions of ether. The ether layers are combined and washed sequentially with sodium bicarbonate, and water. The resulting organic layer is dried (MgSO$_4$), filtered, and concentrated in vacuo to give the crude dibromide (2,4-dibromide-6-tert-butylphenol), which is used in the next reaction without further purification.

A flask with mechanical stirring and a reflux condenser is charged with a mixture of 10% NaOH (117 mL) and zinc (60 g). The crude dibromide from above is added as a solid in small portions. The mixture is heated to 100° C. for 30 min. After cooling to room temperature, the reacted material is filtered, and acidified in an ice bath using 6N HCl. The product is extracted with 3 100 mL portions of ether. The ether extract is washed with water (2×300 mL), dried (MgSO$_4$), filtered, and concentrated in vacuo. The crude product is dissolved in hexane (100 mL) and slurried with 50 g silica gel. The hexane is filtered off, and the silica gel is washed with 100 mL more hexane. The silica gel treatment is then repeated. The combined hexane portions are concentrated in vacuo to give mono-bromide, which is used without further purification in the next step.

To 100 mL tetrahydrofuran (THF), cooled to −78° C. under argon, is added tert-butyllithium (35.4 mL of 1.8M solution), with stirring. A sample of the mono-bromide from above (4.56 g, 20 mmol), dissolved in 5 mL THF, is added dropwise with stirring. After stirring 30 minutes at −78° C., the reaction is warmed to 0° C. and stirred 30 minutes. After re-cooling to −78° C., iodomethane (2.96 mL, 48 mmol) is added dropwise with stirring. The reaction is allowed to warm to 0° C., and stirring is continued for 30 minutes. The reaction is added to 1N HCl (ca 100 mL) and extracted with 3 100 mL portions of ether. The ether portions are combined, dried (MgSO$_4$), filtered, and chromatographed on silica gel (sg) (2% EtOAc in hexane) to give 1.04 g pure 2-tert-butyl-6-methylphenol.

To a solution of 2-tert-butyl-6-methylphenol (1.2 g, 7.3 mmol) in methylene chloride (28 ml, 1.1 equiv.), stirred under argon at −78° C., is added 5-hexynoyl chloride (1.0 g) followed by tin tetrachloride (0.93 mL, 1.1 equiv.). After stirring 30 minutes at −78° C., the reaction is warmed to −50° C. and stirred 5 minutes more. The mixture is then quenched with 1N HCl/ether. The product is extracted from 1N HCl with 3 portions of ether, and the ether layers are combined and washed with water. The resulting ether layer is dried (MgSO$_4$), filtered, and concentrated in vacuo to give 2.14 g crude product. The product is flash chromatographed on silica gel using 10% EtOAc in hexane to give 0.97 g 2-t-butyl-4-(5-hexynoyl)-6-methylphenol. Crystallization from hexane gives crystals, mp 63°–64° C.

IR (CCl4): 3610(s), 3430(m), 3320(s), 2960(s), 2120(w), 1675(s), 1580(s), 1340(m), 1180(s), 630(m), cm$^{-1}$.

$^1$H-NMR (CDCl3)δ(ppm): 1.45(s, 94), 1.98(q, 4H), 2.35(s, 3H), 3.10(t, 2H), 5.60(s, 1H), 7.70 (s, 1H), 7.80(s, 1H); $^{13}$C-NMR (CDCl3) δ: 16.24, 18.00, 23.39, 29.58, 34.73, 36.65, 69.15, 83.86, 123.53, 125.91, 128.80, 129.51, 136.09, 158.04, 199.26 ppm.

EXAMPLE 2

Synthesis of 2-(2-hydroxy-1,1-dimethyl-ethyl)-4-(5′-hexynoyl)-6-t-butylphenol

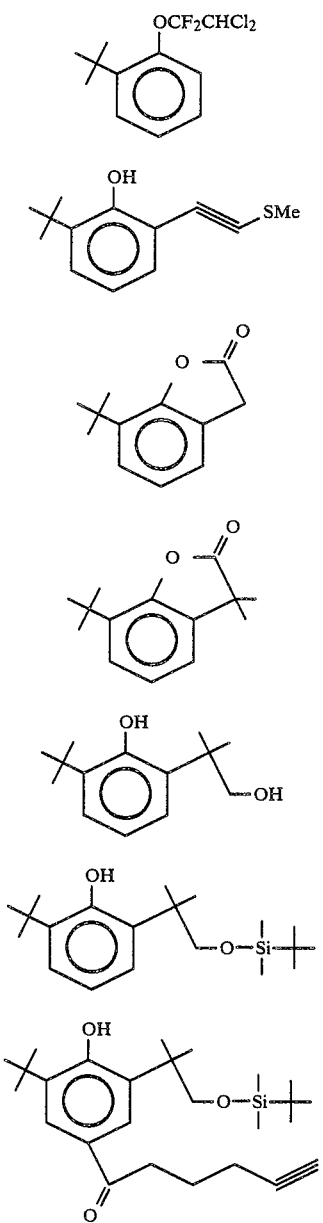

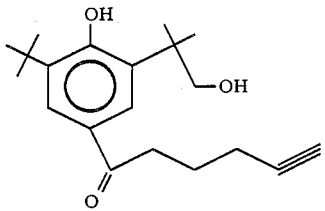

To a mixture of 47.5 g (316 mmol) of o-(t-butyl)-phenol, 91 mL of 40% KOH, and 13 mL of 40% tetra-n-butylammonium hydroxide is added at 0° a solution of ca. 100 mL of 1,1-dichloro-2,2-difluoro-ethylene in 250 mL of CH2Cl2. The flask is well-stoppered at 0° and the mixture is allowed to warm to room temperature and is stirred vigorously for 48 h. The reaction mixture is poured into water and extracted with pet. ether. The combined organic phase is washed with sat. NaCl and dried (MgSO4). Concentration and short-path distillation gives 83.4 g of 2: bp 95°/1 torr; IR (film): 2970 (m), 1445 (m), 1310 (s), 1265 (s), 1235 (s), 1175 (s), 1165 (s), 835 (s), 755 (s) cm$^{-1}$; $^1$H-NMR (CDCl3, TMS)δ: 1.40 (s, 9H), 5.95 (t, J=7 Hz, 1H), 7.0–7.5 (m, 4H).

A solution of 82.2 g (291 mmol) of 2 in 875 mL of tetrahydrofuran (THF) is treated at −78° C. with 640 mL (1.75 mol) of 2.74M nBuLi, keeping the temperature below −60° C. The mixture is stirred at −78° C. for 6 hours and then is allowed to warm very slowly to room temperature where it is stirred overnight. The reaction is cooled back to −78° C. and to it is added 41.1 g (436 mmol) of methyl disulfide. The solution is allowed to warm to 25° C., stirred for 2 hours, and is then poured into 0.1N HCl. The aqueous portion is extracted with ether and the combined organic phase is washed with sat. NaHCO3 and sat. NaCl, and then dried (MgSO4). GC examination of the reaction mixture reveals a very clean reaction, showing very little else besides 3. The volatile solvents are removed in the hood by distillation, with the pot temperature reaching ca. 110° C. GC analysis at this point shows an ca. 3:1 mixture of 3 and the corresponding thioester derived from hydration of the triple bond. Kugelrohr distillation (oven temp.=110°–140° C., 0.5 torr) affords 43.5 g of an approx. 3:1 mixture of 3 and the respective thioester: (Spectra of pure 3) IR (neat): 3480 (m), 2960 (m), 1430 (s), 1225 (m), 745 (s) cm$^{-1}$; $^1$H-NMR (CDCl3, TMS)δ: 1.45 (s, 9H), 2.50 (s, 3H), 6.25 (s, 1H), 6.80 (m 1H), 7.25 (m, 2H).

A mixture of 43.5 g (ca. 193 mmol) of 3 (containing 25% thioester) and 600 mL each of methanol and 3N H2SO4 is refluxed overnight. The reaction solution is concentrated to ca. one-half of its original volume by distilling away the volatiles, and then is cooled to 25° C. and concentrated by means of a water aspirator in the hood (this procedure removes all volatile sulfur-containing by-products). The concentrated reaction is poured into water and extracted with ether. The combined organic phase is washed with sat. NaHCO3 and sat. NaCl, and then dried (MgSO4). The volatiles are removed under reduced pressure and the crude lactone is recrystallized from hexane to afford 23.2 g of pure 4. The mother liquor is flash chromatographed (10% EtOAc/hex) to afford an additional 2.01 g of 4. Total yield of 4 is 25.2 g: mp 99.5°–100°; IR (CDCl3): 2965 (s), 1795 (vs), 1430 (s), 1085 (s), 1070 (s) cm$^{-1}$; $^1$H-NMR (CDCl3, TMS) δ: 1.40 (s, 9H), 3.65 (s, 2H), 7.15 (m, 3H);

13C-NMR (CDCl3, TMS) δ: 29.50, 32.56, 34.19, 122.15, 123.54, 123.90, 125.81, 134.16, 152.65, 174.03.

To a solution of 3.80 g (20.0 mmol) of 4 and 5.0 mL (80 mmol) of iodomethane in 100 mL of THF is added dropwise at 0° C. 5.6 g (50 mmol) of potassium t-butoxide. The mixture is stirred at 0° C. for 30 min and then is warmed to 25° C. and stirred for an additional 2 hours. The reaction is poured into 0.1N HCl and the aqueous layer is extracted with ether. The combined organic phase is washed with sat. NaHCO3 and sat. NaCl, and then dried (MgSO4). The crude, concentration reaction mixture is recrystallized from hexane to afford 2.21 g of pure 5. The mother liquor is Kugelrohr distilled (oven temp=160° C., 0.5 torr) to provide an additional 1.19 g of 5. The total yield of 5 is 3.40 g: mp 84°-85°; IR (CDCl3): 2970 (s), 1795 (vs), 1430 (s), 1280 (s), 1055 (s) cm$^{-1}$; $^1$H-NMR (CDCl3, TMS) δ: 1.40 (s, 9H), 1.50 (s, 6H), 7.15 (m, 3H); —C-NMR (CDCl3 TMS)· δ: (off-resonance multiplicity) 25.38 (q), 29.58 (q), 34.21 (s), 42.09 (s), 120.32 (d), 124.14 (d), 125.59 (d), 134.13 (s, two carbons), 150.11 (s), 180.82 (s).

A solution of 1.14 g (30.0 mmol) of lithium aluminum hydride in 50 mL of ether is treated at 0° C. with 5.45 g (25.0 mmol) of 5. The reaction mixture is warmed to 25° C. and stirred for 1 hour. The excess hydride is decomposed at 0° C. with 25 mL of ethyl acetate followed by 100 mL of a 1:1 mixture of sat. NH4Cl and water. The reaction is filtered through a short pad of celite, washing it well with ether. The combined organic layer is washed with sat. NaCl and dried (MgSO4). Concentration leaves essentially pure 6: mp 67°-68° C.; IR (CCl4): 3640 (m), 3290 (s, br), 2960 (s), 1425 (m), 1385 (m), 1245 (m), 1030 (m) cm$^{-1}$; $^1$H-NMR (CDCl3, TMS) δ: 1.40 (s, 15H), 1.85 (br s, alcoholic OH, 1H), 3.65 (br s, 2H), 6.6-7.3 (m, 3H), 9.05 (s, phenolic OH, 1H); $^{13}$C-NMR (CDCl3, TMS)δ(off-resonance multiplicity): 25.45 (q), 29.99 (q), 34.97 (s), 39.75 (s), 74.13 (t), 118.96 (d), 125.25 (d), 125.58 (d), 133.33 (s), 138.25 (s), 155.28 (s).

To a mixture of 2.81 g (12.7 mmol) of 6, 2.37 g (15.8 mmol) of t-butyldimethylchloro silane, and 0.38 g (3.2 mmol) of 4-dimethylaminopyridine in 60 mL of methylene chloride is added, at room temperature, 5.23 mL (38.0 mmol) of triethylamine. The reaction mixture is stirred overnight at 25° C. and is then poured into water. The aqueous layer is extracted with ether and the combined organic layer is washed with sat. NaCl and dried (MgSO4). The crude, concentrated reaction solution is flushed through a short column of silica gel eluting with 2% EtOAc/hex (R$_f$ of 9=0.72) directly into a round-bottomed flask. Concentration affords 4.06 g of 9: IR (film): 3225 (s, br), 2950 (s), 2930 (s), 1385 (s), 1250 (s), 1050 (s), 835 (s), 780 (s) cm$^{-1}$; $^1$H-NMR (CDCl3, TMS)δ: 0.15 (s, 6H), 0.95 (s, 9H), 1.45 (s, 15H), 3.70 (s, 2H), 6.6-7.3 (m, 3H), 9.50 (s, 1H).

A solution of 4.38 g (13.0 mmol) of 9 in 70 mL of methylene chloride is sequentially treated at −78° C. with 1.85 g (14.3 mmol) of 5-hexynoyl chloride and 1.68 mL (14.3 mmol) of stannic chloride. The mixutre is stirred at −78° C. for one hour and is then allowed to warm up to ca. −50° C. and stirred there for 5 min. The reaction is poured into 0.1N HCl and the layers are separated. The aqueous portion is extracted with ether and the combined organic phase is washed with sat. NaHCO3 and sat. NaCl, and then dried (MgSO4). TLC (10% EtOAc/hexane) showed only a trace of 9 (R$_f$=0.70) along with the nearly pure 10 (R$_f$=0.38). The crude, concentrated 10 is diluted with 75 mL of THF and to it is added at 25° C., 8.19 g (26.0 mmol) of tetra-n-butylammonium fluoride trihydrate. After stirring the mixture for one hour at 25° C. it is poured into water and the aqueous layer is extracted with ether. The combined organic phase is washed with sat. NaCl and dried (MgSO4). TLC (20% EtOAc/hexane) shows predominantly 11 (R$_f$=0.22), with no 10 (R$_f$=0.60) remaining. Flash chromatography affords 3.21 g of 11: mp 91°-93°; IR (CHCl3): 3620 (m), 3310 (s), 3200 (m, br), 2970 (s), 2110 (w), 1655 (s), 1585 (s), 1270 (s), 635 (m) cm$^{-1}$; $^1$H-NMR (CDCl3, TMS)δ: 1.40 (s, 15H), 1.7-2.3 (m, 5H), 3.05 (t, 2H), 3.80 (d, 2H), 5.40 (t, 1H), alcoholic OH), 7.80 (s, 2H), 10.95 (s, 1H), phenolic OH); $^{13}$C-NMR (CDCl3, TMS) δ (off-resonance multiplicity): 18.03 (t), 23.71 (t), 25.38 (q), 29.68 (q), 35.25 (s), 36.58 (t), 40.06 (s), 69.22 (d), 73.55 (t), 83.73 (s), 126.40 (d), 126.69 (d), 127.06 (s), 133.92 (s), 138.34 (s), 161.54 (s), 200.91 (s).

EXAMPLE 3

Synthesis of 1-Allyl-4-(5'-hexynoyl)-6-t-butylphenol

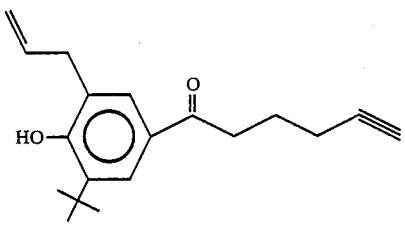

To a stirred solution of o-(t-butyl)-phenol (11.3 g; 75 mmol) in acetone (150 ml) is added allyl bromide (10.9 g, 1.2 equiv.) and anhydrous K2CO3. After stirring 18 hr at reflux, the reaction is added to water (200 ml) and extracted with 3×150 ml portions of petroleum ether. The combined organic layers are dried (MgSO4), filtered, and concentrated in vacuo to give the crude product, which is purified by silica gel (sg) chromatography (hexane elution) to yield 1-prop-2-enyloxy-2-t-butylbenzene (11.6 g; 81% yield).

A glass lined 3 L vessel is charged with 1-prop-2-enyloxy-2-t-butylbenzene (11.6 g; 61 mmol), Ac2O (160 ml), and NaOAc (10 g). After heating at 200° C. for 18 hr, the mixture is poured into 200 g ice, with stirring for 15 min. It is then extracted with 3×300 ml portions of ether. The combined ether layers are slowly added to an ice-cooled flask containing NaHCO3 and stirred for 40 min. The ether layer is then separated, washed with 2×300 ml saturated NaCl solution, dried (MgSO4), filtered, and concentrated in vacuo to give 17.2 g crude product. Chromatography using 3:1 petroleum ether/CH2Cl2 then gives 7.69 g pure 1-acetoxy-2-allyl-6-t-butylbenzene (54% yield).

To a solution of 1-acetoxy-2-allyl-6-t-butylbenzene (7.69 g) in dry ether (66 ml) is added lithium aluminum hydride (LAH) (2.2 g) with stirring. After 30 minutes at reflux, the reaction is acidified using 3N HCl (ca. 75 ml) with ice bath cooling. The mixture is then poured into water (200 ml) and extracted with 3×100 ml ether. The ether layers are combined, dried (MgSO4), filtered, and concentrated in vacuo to give 5.4 g product, which is purified by silica gel chromatography (50:1 ether/CH2Cl2) to give pure 2-allyl-6-t-butylphenol (4.69 g; 76% yield).

A solution of 2-allyl-6-t-butylphenol (0.57 g; 3 mmol) in dry CH2Cl2 (12 ml) is cooled to −78° C., and 5-hexynoyl chloride (0.43 g; 3.3 mmol) is added via syringe, followed by SnCl4 (0.375 ml) added dropwise via syringe, with stirring under Argon. After 30 min the reaction is allowed to warm to 0° C. and is stirred at that temperature for 5 min; it is then quenched with ca 1 ml of 3N HCl. The reaction is poured into 100 ml water and extracted with 3×50 ml portions of ether. The combined ether layers are washed with 150 ml portions of water until the aqueous layer is neutral (pH test). The ether layer is dried (MgSO4), filtered, and concentrated in vacuo to give crude product, which is chromatographed with 20:1 hexane/EtOAc, giving 0.64 g 2-allyl-4-(5-hexynoyl)-6-t-butylphenol (77% yield). The product is recrystallized from hexane at 0° C. to give crystals melting at 62°–63° C.

$^{13}$C-NMR (CDCl3)δppm: 18.0, 23.3, 29.6, 34.7, 35.9, 36.6, 69.0, 83.9, 117.9, 124.8, 126.5, 129.0, 129.4, 135.6, 136.9, 158.2, 198.9.

IR (CCl4): 3500 cm$^{-1}$ (m), 3300 (m), 2950 (s), 2100 (w), 1665 (s), 1580 (m), 1410 (m), 1360 (m), 1310 (m), 1250 (m), 1180 (s), 1140 (m), 920 (m).

$^{1}$H-NMR (CDCl3) (60 mH2) δ ppm: 1.45 (s, 9H), 1.8–2.4 (m, 5H), 3.15 (t, 2H), 3.60 (d, 2H), 5.1–5.4 (m, 1H), 6.08 (s, 1H), 7.80 (d, 1H), 8.0 (d, 1H).

GC/EI: C19H24O2.

MS: M+ at 284.

EXAMPLE 4

Synthesis of 2-n-propyl-4-(5'-hexynoyl)-6-t-butylphenol

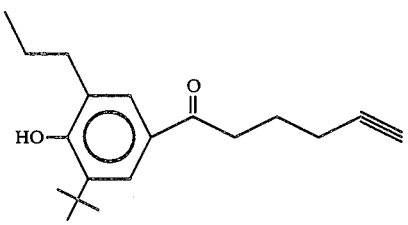

A solution of 2-allyl-6-t-butylphenol (1.9 g) (see Example 3) in 100 ml MeOH is hydrogenated in a Parr system for 75 min at 25° C. (50 psi of H2). The mixture is then filtered and concentrated in vacuo to give 2-n-propyl-6-t-butylphenol (1.88 gram; 98% yield), which is used without further purification in the next step.

2-n-propyl-6-t-butylphenol is converted to 2-n-propyl-4-(5'-hexynoyl)-6-t-butylphenol following the analogous procedure in Example 3 above. mp=89°–90° C.

$^{13}$C-NMR (CDCl3) δ ppm: 14.0, 18.1, 23.4, 22.8, 29.7, 32.1, 34.8, 36.6, 69.0, 83.9, 125.8, 127.7, 128.5, 129.1, 136.0, 157.3, 199.3 ppm.

IR (CCl4): 3600 cm$^{-1}$ (m), 3300 (m), 2980 (s), 2860 (m), 2100 (w), 1710 (w), 1670 (s), 1580 (m), 1415 (m), 1360 (m), 1320 (m), 1265 (m), 1170 (m).

$^{1}$H-NMR (CDCl3) (60 mH2) δ ppm: 1.08 ppm (t, 3H), 1.45 ppm (s, 9H), 1.8–2.5 ppm (m, 7H tot.), 2.50–2.85 (m, 2H), 3.17 (t, 2H), 6.0 (s, 1H), 7.80 (d, 1H), 7.90 (d, 1H).

GC/EI: C19H26O2.

MS: M+ at 286.

EXAMPLE 5

2-s-(3-butenyl)-4-(5'-hexynoyl)-6-t-butylphenol

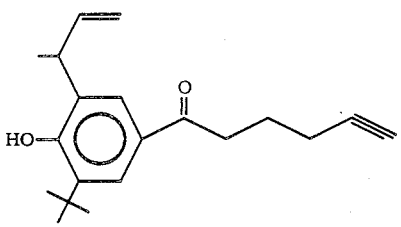

o-(t-Butyl)-phenol is converted into 2-s-(3-butenyl)-6-t-butylphenol by procedures analogous to those in Example 3 above. Continuing to follow procedures analogous to those in Example 3, 2-s-(3-butenyl)-6-t-butylphenol is converted to the product, 2-s-(3-butenyl)-4-(5-hexynoyl)-6-t-butylphenol, mp 52°–53° C.

$^{13}$C-NMR (CDCl3) δ ppm: 18.0, 18.7, 23.3, 29.7, 36.1, 36.6, 38.8, 69.2, 83.9, 115.9, 126.3, 126.6, 129.4, 129.7, 137.4, 141.8, 157.9, 198.9.

IR (CCl4): 3470 (m), 3300 (m), 2960 (s), 2100 (w), 1670 (s), 1560 (m), 1410 (m) 1350 (m), 1180 (s), 980 (m), 920 (m), 900 (m).

$^{1}$H-NMR (CDCl3) δ ppm: 0.9–1.6 (m, 12H), 2.0–2.5 (m, 5H), 3.10 (t, 2H), 3.59–3.8 (m, 1H), 5.18–5.5 (m, 2H), 5.9–6.5 (m, 1H), 6.1 (s, 1H), 7.8 (d, 1H), 8.0 (d, 1H).

GC/EI: C20 H26 O2.

MS: M+ at 298.

EXAMPLE 6

2-s-butyl-4-(5'-hexynoyl)-6-t-butylphenol

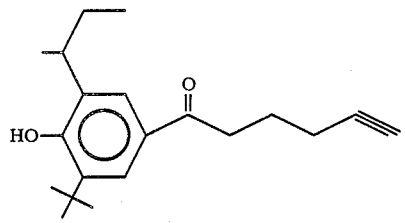

o-(t-Butyl)-phenol is converted to 2-s-(3-butenyl)-6-t-butylphenol by procedures analogous to those in Example 3 above. Hydrogenation following procedures analogous to those in Example 4 then gives 2-s-butyl-6-t-butylphenol. The final transformation, using procedures analogous to those in Example 3, yields 2-s-butyl-4-(5'-hexynoyl)-6-t-butylphenol, mp 96°–97° C.:

$^{13}$C-NMR (CDCL3) δ ppm: 12.1, 18.1, 20.6, 23.5, 29.8, 30.2, 33.9, 34.8, 36.6, 69.1, 83.9, 125.4, 129.3, 132.8, 135.9, 156.8, 199.2.

$^{1}$H-NMR (CDCl3) δ ppm: 0.92 (t, 3H), 1.3–1.5 (m, 12H), 1.6–2.7 (m, 7H), 3.1 (m, 3H), 5.8 (s, 1H), 7.8 (d, 1H), 7.9 (d, 1H).

GC/EI: C20H28O2.

MS: M+ at 300.

EXAMPLE 7

2-n-propyl-4-(6'-heptynoyl)-6-t-butylphenol

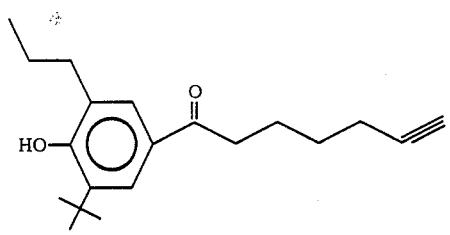

Intermediate 2-n-propyl-6-t-butylphenol is reacted with acetyl chloride, using the conditions outlined in Example 3 above, to give 2n-propyl-4-acetyl-6-t-butylphenol. This compound is then converted to 2-n-propyl-4-(6'-heptynoyl)-6-t-butylphenol according to the following procedure:

A solution of 2.24 ml (16.0 mmol) of diisopropylamine in 75 ml of THF is treated at −78° C. with 5.36 ml (15.0 mmol) of 2.80M n-butyllithium. The solution is warmed to 0° C. and stirred for an additional 15 minutes, then is cooled back to −78° C. and to it is added 7.25 mmol of 2-n-propyl-4-acetyl-6-t-butylphenol. The reaction mixture is allowed to warm to 0° C. and is stirred for 30 minutes. The viscous white slurry is then treated successively with 5.0 ml of hexamethylphosphoramide and 0.83 g (8.0 mmol) of 5-chloro-1-pentyne and is then allowed to warm to 25° C., where it is stirred for one hour. The reaction mixture is poured into 1N HCl and the layers are separated. The aqueous portion is extractd with pentane and the combined organic phase is washed with 1N HCl, saturated NaHCO3, saturated NaCl and then dried (MgSO4). The concentrate is purified by flash chromatography (10% EtOAc/hexane, $R_f=0.33$) and recrystallization (heptane) to provide the title compound.

EXAMPLE 8

4-(3',3'-dimethoxypropionyl)-2-s-butyl-6-t-butylphenol

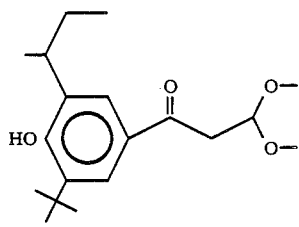

A mixture of Mg (10 mmol), 2-s-butyl-4-bromo-6-t-butyl-1-trimethylsiloxy benzene [which is prepared from 2-s-butyl-6-t-butylphenol by sequential reactions with bromine (CH2Cl2, 0° C., 15 min) and n-butyllithium (THF, −78° C., 15 min)/chlorotrimethylsilane (−78° C. to −25° C., 18 hr)] and a few drops of 1,2-dibromoethane in 25 ml THF is heated at reflux for two hr and then is added to an excess of pulverized dry ice. The resulting slurry is stirred for 1 hr, then added to a 300 ml portion of 1N NaOH and stirred for 1 hr. The resulting mixture is washed with 3×100 ml portions of ether, and then is made acidic with excess 3N HCl. The product is extracted with 3×200 ml portions of ethyl acetate. The combined organic portions are dried (MgSO4), filtered, and concentrated in vacuo to give 3-s-butyl-4-hydroxy-5-t-butylbenzoic acid, used in the next step without further purification.

A solution of 20 mmol of bis(trimethylsilyl)acetylene and 15 mmol of 2-s-butyl-6-t-butyl-4-hydroxybenzoyl chloride [which is prepared from 3-s-butyl-4-hydroxy-5-t-butylbenzoic acid by treatment with oxalyl chloride (benzene, 60° C., 2 hr)] in 80 ml CH2Cl2 is treated at −78° C. for 30 min, and is then poured into 3N HCl. The product is extracted with pentane (3×200 ml) and the combined organic portion is washed with saturated NaCl, dried over MgSO4, filtered, and concentrated in vacuo. The crude product, dissolved in 80 ml THF, plus 200 ml MeOH, is treated with 200 ml 1N KOH. After stirring at 25° C. for 18 hr, the reaction is poured into 1N HCl and extracted with 3×200 ml portions of ether. The combined organic portion is washed with saturated NaCl, dried over MgSO4, filtered, and concentrated in vacuo. The product is purified by chromatography on sg with 10% EtOAc/hexane to yield pure 4-(3',3'-dimethoxypropionyl)-2-s-butyl-6-t-butylphenol.

EXAMPLE 9

4-(1'-hydroxy-5'-hexynyl)-2-s-butyl-6-t-butylphenol

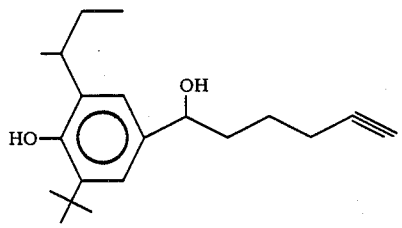

A mixture of Mg (10 mmol), 5 mmol of 2-s-butyl-4-bromo-6-t-butyl-1-trimethylsiloxybenzene [which is prepared from 2-s-butyl-6-t-butylphenol by sequential reactions with bromine (CH2Cl2, 0° C., 15 min) and n-butyllithium (THF, −78° C., 15 min)/chlorotrimethylsilane (−78° C. to −25° C., 18 hr)] and a few drops of 1,2-dibromoethane in 25 ml THF is heated at reflux for two hr and then is cooled to −78° C. To it is added 4.5 mmol of hex-5-ynal [which is prepared from the oxidation of hex-5-yn-1-ol using pyridinium chlorochromate]. The reaction is stirred at −78° C. for 15 min and then is allowed to warm to 0° C. where it is stirred an additional 30 min. The mixture is poured into saturated NH4Cl and extracted with pentane. The combined organic portion is washed with saturated NaCl, and dried over MgSO4. The crude silylated intermediate is concentrated, dissolved in 50 ml THF, and is treated at 25° C. with 6.25 mmol of tetra-n-butyl-ammonium fluoride trihydrate. After stirring for 1 hr, the mixture is poured into saturated NH4Cl and extracted with pentane. The combined organic portion is washed with saturated NaCl, dried over MgSO4, filtered, and concentrated in vacuo. The concentrate is purified by sg chromatography to give pure 4-(1'-hydroxy-5'-hexynyl)-2-s-butyl-6-t-butylphenol.

EXAMPLE 10

2-i-Propyl-4-(3'-butynoyl)-6-t-butylphenol

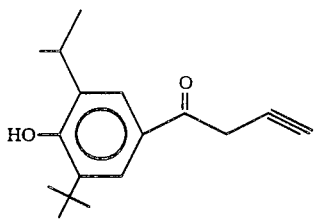

3-i-Propyl-4-hydroxy-5-t-butylbenzoic acid, prepared by similar methods as described for 3-s-butyl-4-hydroxy-5-t-butyl benzoic acid in Example 8, is converted to its acid chloride by treatment with oxalyl chloride (benzene, 60° C., 2 hr).

A solution of 14.0 mmol of 3-s-butyl-5-t-butyl-4-hydroxybenzoyl chloride in 35 ml of benzene is treated successively at 0° C. with 3.68 g (11.2 mmol) of allenyltributyltin (which is prepared from reaction of the Grignard reagent derived from propargyl bromide with tri-n-butyltin chloride) and 0.05 g (0.4 mmol) of zinc chloride. The mixture is stirred at 0° C. for 20 minutes and then at room temperature for 30 minutes. A small amount (1–2 ml) of formic acid is then added to the reaction mixture and it is then concentrated. Purification by flash chromatography (10% ether/petroleum ether containing 0.5% formic acid) and recrystallization (hexane containing 0.5% formic acid) affords the title compound, which contains about 10% of the isomeric 4-butadienoyl-2-s-butyl-6-t-butylphenol.

EXAMPLE 11

2-Allyl-4-(4'-pentynoyl)-6-t-butylphenol

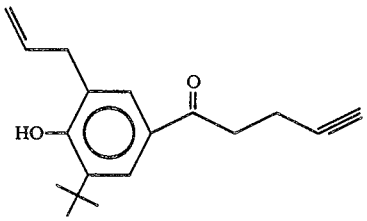

2-Allyl-6-t-butylphenol, upon reaction with 4-pentynoyl chloride [which is made from 4-pentynoic acid using the procedure in Example 12] by methods analogous with those of Example 3, gives 2-allyl-4-(4'-pentynoyl)-6-t-butylphenol.

EXAMPLE 12

2-s-butyl-4-(5'-hexenoyl)-6-t-butylphenol

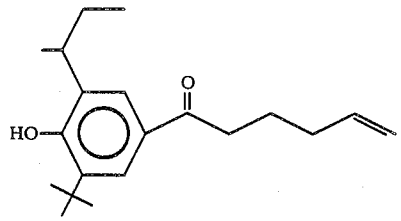

The Grignard reagent made from 6 mmol of 2-s-butyl-6-t-butylphenol (as previously described in Example 9) is cooled to 0° C. and added to a mixture of 8 mmol of zinc chloride in 25 ml THF. The resulting slurry is stirred at 25° C. for 15 minutes, and then is treated successively with 5 mol % of tetrakis(triphenylphosphine)-palladium and 5 mmol of 5-hexenoyl chloride [which is prepared by sequential treatment of 5-hexenoic acid in ether with n-butyllithium (5 mmol, 0° C. to 25° C.) and oxalyl chloride (5 mmol, 25° C. to 40° C.) and used in situ]. After stirring at 25° C. for 1 hr, the mixture is poured into saturated NH4Cl and extracted with pentane. The combined organic portion is washed with saturated NaCl, dried over MgSO4, and filtered. After concentrating in vacuo, the mixture is dissolved in 25 ml of THF plus 25 ml MeOH and is then treated at 25° C. with 5 ml 1N KOH. After stirring 1 hr, the mixture is poured into 1N HCl. The aqueous portion is extracted with pentane and the combined organic portion is washed with saturated NaCl, dried over MgSO4, filtered, and concentrated in vacuo. Chromatography on sg (5% EtOAc/hexane) gives pure 2-s-butyl-4-(5'-hexenoyl)-6-t-butylphenol.

EXAMPLE 13

2-methyl-4-(5'-hexynoyl)-6-trifluoromethylphenol

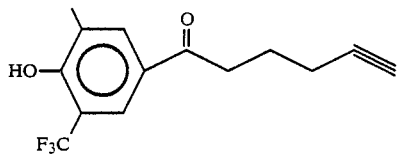

To a solution of o-trifluoromethylphenol (3.0 g; 19 mmol) in CH2Cl2 (20 ml) is added bromine (6.4 g; 39.9 mmol) at 25° C. with stirring, and stirring is continued for 2.5 hours. The reaction is then poured into a separatory funnel with 100 ml of water plus 100 ml ether. The aqueous portion is extracted with 3×100 ml portions of ether. The organic fractions are combined and washed with 1M sodium bicarbonate (300 ml) followed by a water (200 ml) wash. The mixture is then dried (MgSO4), filtered, and concentrated in vacuo to give 5.8 g crude 2,4-dibromo-6-trifluoromethylphenol. To remove contaminating mono-brominated material, the reacting above is repeated on the crude product (6.4 g bromine) to give pure product (5.77 g of 2,4-dibromo-6-trifluoromethylphenol) used in the next step without further purification.

A solution of 2,4-dibromo-6-trifluoromethylphenol (5.77; 18 mmol) is dissolved in dry THF (45 ml), and s-butyllithium (21 ml of 1.7M solution) is added dropwise with stirring at −78° C. under argon. After stirring at −78° C. for 30 minutes, the mixture is allowed to warm to 0° C. and is stirred 40 minutes more. The reaction is quenched with 1N HCl and extracted from 1N HCl (50 ml) with 3×50 ml portions of ether. The combined ether portions are washed with 1M sodium bicarbonate (100 ml) then dried (MgSO4), filtered and concentrated in vacuo to give 3.84 g crude product. Chromatography on silica gel (95:5 petroleum ether/ether) thus gives 2-bromo-6-trifluoromethylphenol.

t-Butyllithium (1.7 ml of a 1.8M solution of hexane; 3 equiv.) is added to THF (1 ml) and cooled to −78° C. under argon with stirring, and a solution of 2-bromo-6-trifluoromethylphenol in dry THF (1 ml; 1 mmol) is added dropwise via syringe. The reaction is stirred 30 minutes, and then iodomethane (340 mg; 2.4 equiv.) is added dropwise via syringe at −78° C. under argon, with stirring. The mixture is allowed to warm to 0° C. with stirring over 15 minutes, and stirring is continued for 45 minutes more. The reaction is then quenched with 1N HCl (3 ml) and extracted from 1N HCl (10 ml) with 3×10 ml portions of ether. The combined ether portions are washed with water (3×20 ml portions: pH tests neutral), and the solution is then dried (MgSO$_4$), filtered, and concentrated in vacuo to give crude 2-methyl-6-trifluoromethylphenol, which is chromatographed on silica gel with 5% ether in petroleum ether to give pure product.

The resulting 2-methyl-6-trifluoromethylphenol is converted to 2-methyl-4-(5'-hexynoyl)-6-trifluoromethylphenol by reaction with 5-hexynoyl chloride using a Friedel Craft reaction as described in Example 3 above.

EXAMPLE 14

Carrageenan Rat Paw Edema Test

Male Sprague-Dawley rats (Charles River Laboratories) are weighed and food fasted overnight. The animals are then divided into four to six groups of six animals each according to body weights (average about 145 g) so that each group has about the same average body weight (within 10 g).

The following morning animals are dosed with the test compound and then placed in individual cages. For oral dosing, the drug is suspended in 0.5% methyl cellulose with 2% Tween 80, and delivered via stomach tube in a 5 ml volume.

Paw volumes (0 time) are determined on both hind paws with a mercury displacement device equipped with a transducer and digitizer. One hour after dosing the test compound, the animals are placed in a plastic restrainer and 50 ul of a 1% (w/w) carrageenan solution in 0.9% saline is injected into the ventral surface of the left rear paw. Four hours after the carrageenan injection, the paw volumes are again determined.

The results are expressed as percent inhibition of the mean paw volume of the test group relative to the control group. Statistical differences are determined by one way analysis of variance.

TABLE 1

| Carrageenan Rat Paw Edema Test Results | |
|---|---|
| Title Compound of Example No. | Percent Inhibition at 100 mg/kg dosed P.O* |
| 1 | 75.4 |
| 2 | 48.4 |
| 3 | 65.8 |
| 4 | 53.2 |
| 5 | 90.8 |
| 6 | 51.5 |

*All values are statistically significant from control at P ≦ 0.05.

EXAMPLE 15

Pharmaceutical Compositions in Tablet Form

Tablets are prepared by conventional methods, such as mixing and direct compaction, formulated as follows:

| Ingredient | mg per tablet |
|---|---|
| Title Compound of Example 1 | 200 |
| Microcrystalline cellulose | 100 |
| Sodium starch glycolate | 30 |
| Magnesium stearate | 3 |

When administered orally two times daily, the above composition significantly reduces the inflammation in a patient suffering from rheumatoid arthritis. A significant benefit is also achieved by twice daily administration of this composition to a patient suffering from osteoarthritis.

Similar results are achieved with tablets formulated as above but replacing the 200 mg of the title compound of Example 1 with: 300 mg of the title compound of Example 3; 400 mg of the title compound of Example 2; 350 mg of the title compound of Example 4; or 100 mg of the title compound of Example 5.

EXAMPLE 16

Pharmaceutical Compositions in Capsule Form

Capsules are prepared by conventional methods, comprised as follows:

| Ingredient | mg per capsule |
|---|---|
| Title Compound of Example 1 | 200 |
| Lactose | To fill to volume of capsule |

The above capsule administered orally once a day substantially reduces the symptomology in a patient afflicted with rheumatoid arthritis or osteoarthritis. Similar results are achieved with capsules formulated as above but replacing the title compound of Example 1 with the title compounds of Examples 1–13.

While particular embodiments of the present invention have been described, it will be obvious to those skilled in the art that various changes and modifications to the compounds and compositions disclosed herein can be made without departing from the spirit and scope of the invention. It is intended to cover, in the apended claims, all such modifications that are within the scope of this invention.

What is claimed is:

1. A compound having the structure:

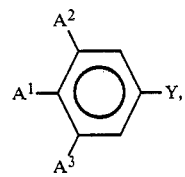

wherein:
(a) —A$^1$ is selected from the group consisting of —OH, —H, and —O$_2$CR; wherein —R is a straight or branched chain alkyl group having from 1 to about 10 carbon atoms;
(b) —A$^2$ is selected from the group consisting of unsubstituted or substituted, saturated or unsaturated, straight, branched and cyclic alkyl having from 1 to about 10 carbon atoms; except for C$_4$ to C$_{10}$ straight-chain, saturated alkyl and tert-butyl; wherein substituents of —A$^2$ may be one or more of halo, —OR³, —O₂CR³, —CO₂R³, and —C(O)R³;

(c) —A³ is selected from —C(CH₃)₃, —Si(CH₃)₃, and —CF₃; and (d) —Y is selected from:
(1) —(CR¹₂)ₙ—C≡C—H, wherein n is an integer from 1 to about 6;
(2)

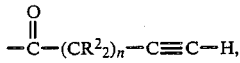

wherein n is an integer from 0 to about 5;
(3)

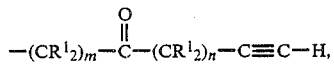

wherein m is an integer from 1 to about 5, and m+n is an integer from 1 to about 5;
(4)

wherein n is 0 or 1;
(5) —(CR¹₂)ₙ—CR³═CH₂, wherein n is an integer from about 2 to about 6;
(6)

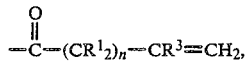

wherein n is an integer from 0 to about 5;
(7)

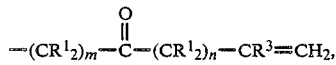

wherein m is an integer from 1 to about 3, and m+n is an integer from 1 to about 3;
(8)

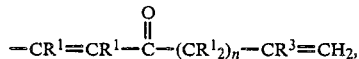

wherein n is an integer from 0 to about 3;
(9) —(CR¹₂)ₙ—CR³═C═CH₂, wherein n is an integer from 0 to about 6;
(10)

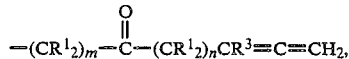

wherein m+n is an integer from 0 to about 5;
(11)

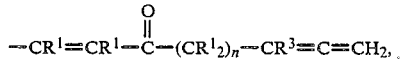

wherein n is an integer from 0 to about 3;

(12) —(CR¹₂)ₙ—CH(ZR⁴)₂, wherein n is an integer from 1 to about 6; and
(13)

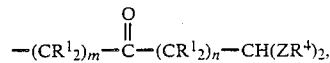

wherein n is an integer from 1 to about 5, m is an integer from 0 to about 4, and m+n is an integer from about 1 to about 5;

and wherein each —R¹ is independently selected from —H, —OR³, —NR³₂, —NR³₃⁺, —N(R³)-C(O)R³, —O₂CR³, —CO₂R³, —C(O)NR³₂, straight or branched chain saturated alkyl group having from 1 to about 3 carbon atoms, and straight or branched chain unsaturated alkyl group having from 1 to about 3 carbon atoms, or two —R¹'s on the same carbon atom are ═O or ═CR³₂; each —R² is independently selected from —H, —OR³, —NR³₂, —NR³₃⁺, —N(R³)C(O)R³, —O₂CR³, —CO₂R³, —C(O)NR³₂, straight or branched chain saturated alkyl group having from 1 to about 3 carbon atoms, and straight or branched chain unsaturated alkyl group having from 1 to about 2 carbon atoms, or two —R²'s on the same carbon atom are ═O or ═CR³₂; each —R³ is independently selected from —H, methyl and ethyl; each —R⁴ is independently selected from —CH₃ and —CH₂CH₃, or the —R⁴'s may be joined to form a cyclic acetal such that both —R⁴'s together are one group selected from —(CH₂)₂— and —(CH₂)₃—; and each —Z— is independently selected from —O—, —S—, —NH—, and —NR⁴—; or the pharmaceutically-acceptable salt thereof.

2. The compound of claim 1 wherein —A¹ is —OH and —A³ is —C(CH₃)₃.

3. The compound of claim 2 wherein —A² is selected from the group consisting of unsubstituted C₁-C₃ saturated, straight-chain alkyl, unsubstituted C₂-C₆ unsaturated, straight-chain alkyl, and unsubstituted C₃-C₆ saturated or unsaturated branched-chain alkyl.

4. The compound of claim 3 wherein:
(a) each —R¹ and —R₂ is independently selected from —H, —OH, methyl, or ethyl, or two —R¹'s or —R²'s on the same carbon atom are ═O or ═CH₂; and wherein further no more than about two —R¹ or —R² groups are a group other than —H;
(b) each —R³ is —H;
(c) each —R⁴ is methyl, or both —R⁴ groups together are the group —(CH₂)₂— which forms a cyclic acetal; and
(d) each —Z— is independently selected from —O— or —S—.

5. The compound of claim 4 wherein the —Y group is selected from:
(1) —(CR¹₂)ₙ—C≡CH, wherein n is an integer from 1 to about 6;
(2)

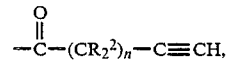

wherein n is an integer from 0 to about 5;
(3)

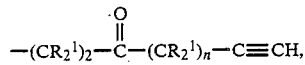

wherein n is an integer from 0 to about 3;

(4)

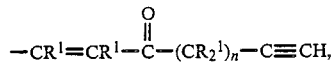

wherein n is 0 or 1;

(5) —(CR$^1_2$)$_n$—CH(ZR$^4$)$_2$, wherein n is an integer from 1 to about 6;

(6)

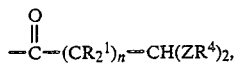

wherein n is an integer from 1 to about 5; and (7)

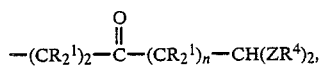

wherein n is an integer from 1 to about 3.

6. The compound of claim 5 wherein each —R$^1$ and —R$^2$ is —H.

7. The compound of claim 5 wherein the —Y group is selected from:

(1)

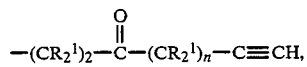

wherein n is an integer from 0 to about 3;

(2)

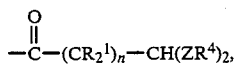

wherein n is an integer from 1 to about 5; and, (3)

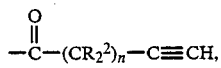

wherein n is an integer from 0 to about 5.

8. The compound of claim 7 wherein each —R$^1$ and —R$^2$ is —H.

9. The compound of claim 2 wherein the —Y group is:

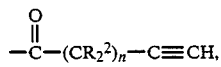

wherein n is an integer from 0 to about 5.

10. The compound of claim 7 wherein the —Y group is:

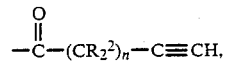

wherein n is an integer from 0 to about 5.

11. The compound of claim 10 wherein each —R$^2$ is —H.

12. The compound of claim 11 wherein n is an integer of from 1 to about 4.

13. The compound of claim 11 wherein n=3.

14. A pharmaceutical composition comprising:
(a) a safe and effective amount of an anti-inflammatory compound of claim 1; and
(b) a pharmaceutically-acceptable carrier.

15. A pharmaceutical composition comprising:
(a) a safe and effective amount of an anti-inflammatory compound of claim 2; and
(b) a pharmaceutically-acceptable carrier.

16. A pharmaceutical composition comprising:
(a) a safe and effective amount of an anti-inflammatory compound of claim 4; and
(b) a pharmaceutically-acceptable carrier.

17. A pharmaceutical composition comprising:
(a) a safe and effective amount of an anti-inflammatory compound of claim 7; and
(b) a pharmaceutically-acceptable carrier.

18. A pharmaceutical composition comprising:
(a) a safe and effective amount of an anti-inflammatory compound of claim 10; and
(b) a pharmaceutically-acceptable carrier.

19. A pharmaceutical composition comprising:
(a) a safe and effective amount of an anti-inflammatory compound of claim 13; and
(b) a pharmaceutically-acceptable carrier.

20. A method for treating diseases characterized by inflammation, said method comprising administering to a human or lower animal in need of such treatment a safe and effective amount of an anti-inflammatory compound of claim 1.

21. A method for treating diseases characterized by inflammation, said method comprising administering to a human or lower animal in need of such treatment a safe and effective amount of an anti-inflammatory compound of claim 2.

22. A method for treating diseases characterized by inflammation, said method comprising administering to a human or lower animal in need of such treatment a safe and effective amount of an anti-inflammatory compound of claim 4.

23. A method for treating diseases characterized by inflammation, said method comprising administering to a human or lower animal in need of such treatment a safe and effective amount of an anti-inflammatory compound of claim 7.

24. A method for treating diseases characterized by inflammation, said method comprising administering to a human or lower animal in need of such treatment a safe and effective amount of an anti-inflammatory compound of claim 10.

25. A method for treating diseases characterized by inflammation, said method comprising administering to a human or lower animal in need of such treatment a safe and effective amount of an anti-inflammatory compound of claim 13.

* * * * *

UNITED STATES PATENT AND TRADEMARK OFFICE
CERTIFICATE OF CORRECTION

Page 1 of 5

PATENT NO. : 4,847,303
DATED : July 11, 1989
INVENTOR(S) : M. E. Loomans, R. S. Matthews and J. A. Miller It is certified that error appears in the above-identified patent and that said Letters Patent is hereby corrected as shown below:

Column 5, lines 24-26, "$-\overset{O}{\underset{\|}{C}}-(CR_2^2)_n-C\equiv CH,$" should be -- $-\overset{O}{\underset{\|}{C}}-(CR^2_2)_n-C\equiv CH,$ --.

Column 5, lines 31-33, "$-(CR_2^1)_2-\overset{O}{\underset{\|}{C}}-(CR_2^1)_n-C\equiv CH,$" should be -- $-(CR^1_2)_2-\overset{O}{\underset{\|}{C}}-(CR^1_2)_n-C\equiv CH,$ --.

Column 5, lines 38-40, "$-CR^1=CR^1-\overset{O}{\underset{\|}{C}}-(CR_2^1)_n-C\equiv CH,$" should be -- $-CR^1=CR^1-\overset{O}{\underset{\|}{C}}-(CR^1_2)_n-C\equiv CH,$ --.

Column 5, lines 48-50, "$-\overset{O}{\underset{\|}{C}}-(CR_2^1)_n-CH(ZR^4)_2,$" should be -- $-\overset{O}{\underset{\|}{C}}-(CR^1_2)_n-CH(ZR^4)_2,$ --.

Column 5, lines 56-58, "$-(CR_2^1)_2-\overset{O}{\underset{\|}{C}}-(CR_2^1)_n-CH(ZR^4)_2,$" should be -- $-(CR^1_2)_2-\overset{O}{\underset{\|}{C}}-(CR^1_2)_n-CH(ZR^4)_2,$ --.

UNITED STATES PATENT AND TRADEMARK OFFICE
CERTIFICATE OF CORRECTION

PATENT NO. : 4,847,303
DATED : July 11, 1989
INVENTOR(S) : M. E. Loomans, R. S. Matthews and J. A. Miller It is certified that error appears in the above–identified patent and that said Letters Patent is hereby corrected as shown below:

Column 5, lines 63-65, "$-(CR_2^1)_2-\overset{O}{\overset{\|}{C}}-(CR_2^1)_n-C\equiv CH,$" should be -- $-(CR^1_2)_2-\overset{O}{\overset{\|}{C}}-(CR^1_2)_n-C\equiv CH,$ --.

Column 6, lines 1-3, "$-\overset{O}{\overset{\|}{C}}-(CR_2^1)_n-CH(ZR^4)_2,$" should be -- $-\overset{O}{\overset{\|}{C}}-(CR^1_2)_n-CH(ZR^4)_2,$ --.

Column 6, lines 11-13, "$-\overset{O}{\overset{\|}{C}}-(CR_2^2)_n-C\equiv CH,$" should be -- $-\overset{O}{\overset{\|}{C}}-(CR^2_2)_n-C\equiv CH,$ --.

Column 14, line 21, "1-Allyl-4-(5'-hexynoyl)-6-t-butylphenol" should be -- 2-Allyl-4-(5'-hexynoyl)-6-t-butylphenol --.

Column 17, line 17, "2n-propyl-4-acetyl-6-t-butyl-" should be -- 2-n-propyl-4-acetyl-6-t-butyl- --.

Column 20, line 48, "reacting" should be --reaction--.

UNITED STATES PATENT AND TRADEMARK OFFICE
CERTIFICATE OF CORRECTION

PATENT NO. : 4,847,303
DATED : July 11, 1989
INVENTOR(S) : M. E. Loomans, R. S. Matthews and J. A. Miller It is certified that error appears in the above-identified patent and that said Letters Patent is hereby corrected as shown below:

Column 24, lines 63-65, "$-\overset{O}{\overset{\|}{C}}-(CR_2^2)_n-C\equiv CH,$" should be -- $-\overset{O}{\overset{\|}{C}}-(CR^2_2)_n-C\equiv CH,$ --.

Column 25, lines 1-3, "$-(CR_2^1)_2-\overset{O}{\overset{\|}{C}}-(CR_2^1)_n-C\equiv CH,$" should be -- $-(CR^1_2)_2-\overset{O}{\overset{\|}{C}}-(CR^1_2)_n-C\equiv CH,$ --.

Column 25, lines 9-11, "$-CR^1=CR^1-\overset{O}{\overset{\|}{C}}-(CR_2^1)_n-C\equiv CH,$" should be -- $-CR^1=CR^1-\overset{O}{\overset{\|}{C}}-(CR^1_2)_n-C\equiv CH,$ --.

Column 25, lines 19-21, "$-\overset{O}{\overset{\|}{C}}-(CR_2^1)_n-CH(ZR^4)_2,$" should be -- $-\overset{O}{\overset{\|}{C}}-(CR^1_2)_n-CH(ZR^4)_2,$ --.

Column 25, lines 25-27, "$-(CR_2^1)_2-\overset{O}{\overset{\|}{C}}-(CR_2^1)_n-CH(ZR^4)_2,$" should be -- $-(CR^1_2)_2-\overset{O}{\overset{\|}{C}}-(CR^1_2)_n-CH(ZR^4)_2,$

UNITED STATES PATENT AND TRADEMARK OFFICE
CERTIFICATE OF CORRECTION

Page 4 of 5

PATENT NO. : 4,847,303
DATED : July 11, 1989
INVENTOR(S) : M. E. Loomans, R. S. Matthews and J. A. Miller It is certified that error appears in the above-identified patent and that said Letters Patent is hereby corrected as shown below:

Column 25, lines 36-39, "$-(CR_2^1)_2-\overset{O}{\underset{\|}{C}}-(CR_2^1)_n-C\equiv CH,$" shuold be -- $-(CR^1_2)_2-\overset{O}{\underset{\|}{C}}-(CR^1_2)_n-C\equiv CH,$ --.

Column 25, lines 43-45, "$-\overset{O}{\underset{\|}{C}}-(CR_2^1)_n-CH(ZR^4)_2,$" should be -- $-\overset{O}{\underset{\|}{C}}-(CR^1_2)_n-CH(ZR^4)_2,$ --.

Column 25, lines 50-53, "$-\overset{O}{\underset{\|}{C}}-(CR_2^2)_n-C\equiv CH,$" should be -- $-\overset{O}{\underset{\|}{C}}-(CR^2_2)_n-C\equiv CH,$ --.

UNITED STATES PATENT AND TRADEMARK OFFICE
CERTIFICATE OF CORRECTION

PATENT NO. : 4,847,303

DATED : July 11, 1989

INVENTOR(S) : M. E. Loomans, R. S. Matthews and J. A. Miller

It is certified that error appears in the above-identified patent and that said Letters Patent is hereby corrected as shown below:

Column 25, lines 60-63, "$-\overset{O}{\overset{\|}{C}}-(CR_2^{\,2})_n-C\equiv CH,$" should be -- $-\overset{O}{\overset{\|}{C}}-(CR^2_{\,2})_n-C\equiv CH$ --.

Column 26, lines 1-3, "$-\overset{O}{\overset{\|}{C}}-(CR_2^{\,2})_n-C\equiv CH,$" should be -- $-\overset{O}{\overset{\|}{C}}-(CR^2_{\,2})_n-C\equiv CH$ --.

Signed and Sealed this

Seventh Day of May, 1991

*Attest:*

*Attesting Officer*

HARRY F. MANBECK. JR.

Commissioner of Patents and Trademarks

UNITED STATES PATENT AND TRADEMARK OFFICE
CERTIFICATE OF CORRECTION

PATENT NO. : B1 4,847,303

DATED : March 12, 1991

INVENTOR(S) : M.E. Loomans, R.S. Matthews and J.A. Miller

It is certified that error appears in the above-indentified patent and that said Letters Patent is hereby corrected as shown below:

Column 1, line 57, "$-\overset{O}{\underset{\|}{C}}-(CR_2^2)_n-C\equiv C-H$" should be -- $-\overset{O}{\underset{\|}{C}}-(CR^2{}_2)_n-C\equiv C-H$ --.

Column 1, line 64, "$-(CR_2^1)_m-\overset{O}{\underset{\|}{C}}-(CR_2^1)_n-C\equiv C-H$" should be -- $-(CR^1{}_2)_m-\overset{O}{\underset{\|}{C}}-(CR^1{}_2)_n-C\equiv C-H$ --.

Column 2, line 4, "$-CR^1=CR^1-\overset{O}{\underset{\|}{C}}-(CR^1{}_2)_n-C\equiv C-H$" should be -- $-CR^1=CR^1-\overset{O}{\underset{\|}{C}}-(CR^1{}_2)_n-C\equiv C-H$ --.

Column 2, line 12, "$-\overset{O}{\underset{\|}{C}}-(CR_2^1)_n-CR^3=CH_2$" should be -- $-\overset{O}{\underset{\|}{C}}-(CR^1{}_2)_n-CR^3=CH_2$ --.

Column 2, line 19, "$-(CR_2^1)_m-\overset{O}{\underset{\|}{C}}-(CR_2^1)_n-CR^3=CH_2$" should be -- $-(CR^1{}_2)_m-\overset{O}{\underset{\|}{C}}-(CR^1{}_2)_n-CR^3=CH_2$ --.

UNITED STATES PATENT AND TRADEMARK OFFICE
CERTIFICATE OF CORRECTION

PATENT NO. : B1 4,847,303

DATED : March 12, 1991

INVENTOR(S) : M.E. Looman, R.S. Matthews and J.A. Miller

It is certified that error appears in the above-indentified patent and that said Letters Patent is hereby corrected as shown below:

Column 2, line 26, "$-CR^1=CR^1-\overset{\overset{O}{\|}}{C}-(CR^1_2)_n-CR^3=CH_2$" should be -- $-CR^1=CR^1-\overset{\overset{O}{\|}}{C}-(CR^1_2)_n-CR^3=CH_2$ --.

Column 2, line 35, "$-(CR^1_2)_m-\overset{\overset{O}{\|}}{C}-(CR^1_2)_n CR^3=C=CH_2$" should be -- $-(CR^1_2)_m-\overset{\overset{O}{\|}}{C}-(CR^1_2)_n CR^3=C=CH_2$ --.

Column 2, line 41, "$-CR^1=CR^1-\overset{\overset{O}{\|}}{C}-(CR^1_2)_n-CR^3=C=CH_2$" should be -- $-CR^1=CR^1-\overset{\overset{O}{\|}}{C}-(CR^1_2)_n-CR^3=C=CH_2$ --.

Column 2, line 51, "$-CR^1_2)_m-\overset{\overset{O}{\|}}{C}-(CR^1_2)_n-CH(ZR^4)_2$" should be -- $-(CR^1_2)_m-\overset{\overset{O}{\|}}{C}-(CR^1_2)_n-CH(ZR^4)_2$ --.

UNITED STATES PATENT AND TRADEMARK OFFICE
CERTIFICATE OF CORRECTION

PATENT NO. : B1 4,847,303                         Page 3 of 3

DATED : March 12, 1991

INVENTOR(S) : M.E. Loomans, R.S. Matthews and J.A. Miller

It is certified that error appears in the above-indentified patent and that said Letters Patent is hereby corrected as shown below:

Column 3, line 2, delete "from 1 to".

Column 3, line 6, after "from" insert --the group consisting of--.

Column 3, line 10, after "from" insert --the group consisting of--.

Column 4, line 33, delete "inflamation" and insert --inflammation--.

Signed and Sealed this

Twenty-fifth Day of October, 1994

Attest:

BRUCE LEHMAN

Attesting Officer                  Commissioner of Patents and Trademarks

REEXAMINATION CERTIFICATE (1433rd)
United States Patent [19]
Loomans et al.

[11] B1 4,847,303
[45] Certificate Issued  Mar. 12, 1991

[54] TERT-BUTYLPHENYL COMPOUNDS USEFUL AS ANTI-INFLAMMATORY AGENTS

[75] Inventors: Maurice E. Loomans; Randall S. Matthews, both of Cincinnati, Ohio; Joseph A. Miller, Baton Rouge, La.

[73] Assignee: The Procter & Gamble Company

Reexamination Request:
No. 90/002,078, Jul. 2, 1990

Reexamination Certificate for:
Patent No.: 4,847,303
Issued: Jul. 11, 1989
Appl. No.: 123,694
Filed: Nov. 23, 1987

[51] Int. Cl.$^5$ ............................................. A61K 31/12
[52] U.S. Cl. ..................... 514/689; 568/662; 568/663; 568/627; 568/337; 568/775; 568/784; 564/366; 564/342; 564/372; 564/374; 564/285; 564/223; 564/169; 562/463; 514/545; 514/546; 514/733; 514/678; 514/649; 514/643; 514/629; 514/621; 514/570; 560/142; 560/130; 558/415; 558/426; 558/427; 558/436; 558/441; 260/410.5
[58] Field of Search .............. 568/662, 663, 627, 775, 568/784, 308, 337; 564/366, 342, 372, 374, 285, 223, 169; 560/142, 130; 558/415, 416, 427, 436, 442; 502/463; 514/689, 545, 546, 733, 678, 644, 643, 629, 621, 570

[56] References Cited
U.S. PATENT DOCUMENTS

| | | | |
|---|---|---|---|
| Re. 27,004 | 12/1970 | Meier et al. | 260/473 |
| 3,226,443 | 12/1965 | Meier et al. | 260/590 |
| 3,322,832 | 5/1967 | Cragoe | 200/592 |
| 3,335,164 | 8/1967 | Scherer et al. | 260/456 |
| 3,477,991 | 11/1979 | Patton et al. | 260/47 |
| 3,526,668 | 9/1970 | Starnes et al. | 260/624 |
| 3,660,505 | 5/1972 | Starnes | 260/619 |
| 3,714,122 | 1/1973 | Kline | 260/62 |
| 3,812,262 | 5/1974 | Chodnekar et al. | 424/282 |
| 4,172,151 | 10/1979 | Moore | 424/330 |

FOREIGN PATENT DOCUMENTS
0256266  2/1988  European Pat. Off. .

Primary Examiner—James H. Reamer

[57] ABSTRACT

The present invention involves compounds having the structure:

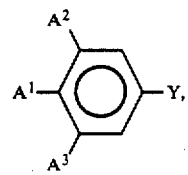

wherein:
(a) —$A^1$ is selected from the group consisting of —OH, —H, and —$O_2CR$;
(b) —$A^2$ is selected from the group consisting of unsubstituted or substituted, saturated or unsaturated, straight, branched and cyclic alkyl having from 1 to about 10 carbon atoms;
(c) —$A^3$ is selected from —$C(CH_3)_3$, —$Si(CH_3)_3$, and —$CF_3$; and
(d) —Y is selected from certain low molecular weight alkyl chains which terminate in specific unsaturated functional groups;

and aldehydes in the form of their acetals; pharmaceutical compositions comprising such compounds; and methods for treating inflammation by administering such compounds.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2-25, dependent on an amended claim, are determined to be patentable.

New Claims 26-29 are added and determined to be patentable.

1. A compound having the structure:

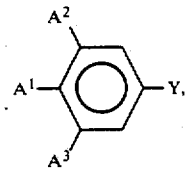

wherein:
(a) —$A^1$ is selected from the group consisting of —OH, —H, and —$O_2CR$; wherein —R is a straight or branched chain alkyl group having from 1 to about 10 carbon atoms;
(b) —$A^2$ is selected from the group consisting of unsubstituted or substituted, saturated or unsaturated, straight, branched or cyclic alkyl having from 1 to 10 carbon atoms; except for $C_4$ to $C_{10}$ straight-chain, saturated alkyl and tert-butyl; wherein substituents of —$A^2$ may be one or more of halo, —$OR^3$, —$O_2CR^3$, —$CO_2R^3$, and —C(O)$R^3$;
(c) —$A^3$ is selected from *the group consisting of* —C(CH$_3$)$_3$, —Si(CH$_3$)$_3$, and —CF$_3$; and
(d) —Y is selected from *the group consisting of:*
(1) —(CR$^1_2$)$_n$—C≡C—H, wherein n is an integer from 1 to about 6;
(2)

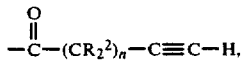

wherein n is an integer from 0 to about 5;
(3)

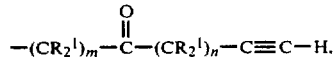

wherein m is an integer from 1 to about 5, and m+n is an integer from 1 to about 5;
(4)

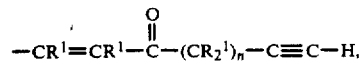

wherein n is 0 or 1; [(5) —(CR$^1_2$)$_n$—CR$^3$=CH$_2$, wherein n is an integer from about 2 to about 6;]
([6] *5*)

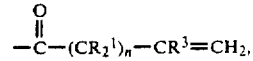

wherein n is an integer from 0 to about 5;
([7] *6*)

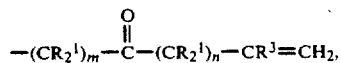

wherein m is an integer from 1 to about 3, and m+n is an integer from 1 to about 3;
([8] *7*)

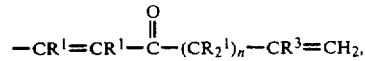

wherein n is an integer from 0 to about 3;
([9] *8*) —(CR$^1_2$)$_n$—CR$^3$=C=CH$_2$, wherein n is an integer from 0 to about 6;
([10] *9*)

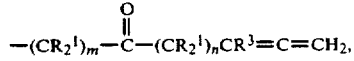

wherein m+n is an integer from 0 to about 5;
([11] *10*)

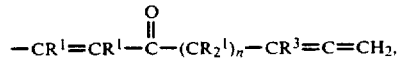

wherein n is an integer from 0 to about 3;
([12] *11*) —(CR$^1_2$)$_n$—CH(ZR$^4$)$_2$, wherein n is an integer from 1 to about 6; and
([13] *12*)

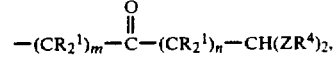

wherein n is an integer from 1 to about 5, m is an integer from 0 to about 4, and m+n is an integer from about 1 to about 5;
and wherein each —$R^1$ is independently selected from *the group consisting of* —H, —$OR^3$, —$NR^3_2$, —$NR^3_3+$, —$N(R^3)C(O)R^3$, —$O_2CR^3$, —$CO_2R^3$, —$C(O)NR^3_2$, straight or branched chain saturated alkyl group having from 1 to about 3 carbon atoms, and straight or branched chain unsaturated alkyl group having from [1] *2* to about 3 carbon atoms, or two —$R^1$'s on the same carbon atom are =O or =CR$^3_2$; each —$R^2$ is independently selected from *the group consisting of* —H, —$OR^3$, —$NR^3_2$, —$NR^3_3+$, —$N(R^3)C(O)R^3$, —$O_2CR^3$, —$CO_2R^3$, —$C(O)NR^3_2$, straight or branched chain saturated alkyl group having from 1 to about 3 carbon atoms, and straight or branched chain unsaturated alkyl group having from 1 to about 2 carbon atoms, or two —R³'s on the same carbon atom are =O or =CR³₂; each —R³ is independently selected from —H, methyl and ethyl; each —R⁴ is independently selected from —CH₃ and —CH₂CH₃, or the —R⁴'s may be joined to form a cyclic acetal such that both —R⁴'s together are one group selected from —(CH₂)₂— and —(CH₂)₃—; and each —Z— is independently selected from —O—, —S—, —NH—, and —NR⁴—; or the pharmaceutically-acceptable salt thereof.

26. A pharmaceutical composition comprising:

(A) a safe and effective amount of an anti-*inflammatory* compound having the structure;

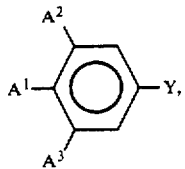

wherein (a) A¹ is selected from the group consisting of —OH, —H, and —O₂CR; wherein R is a straight or branched chain alkyl group having from 1 to about 10 carbon atoms;

(b) A² is selected from the group consisting of unsubstituted or substituted, saturated or unsaturated, straight, branched and cyclic alkyl having from 1 to about 10 carbon atoms; except for C₄ to C₁₀ straight-chain, saturated alkyl and tertbutyl; wherein substituents of —A² may be one or more of halo, —OR³, —O₂CR³, —CO₂R³, and —C(O)R³;

(c) A³ is selected from the group consisting of —C(CH₃)₃, —Si(CH₃)₃, and —CF₃; and (d) Y is —(CR¹₂)ₙ—CR³=CH₂, wherein n is an integer from about 2 to about 6;

and wherein each R¹ is independently selected from the group consisting of —H, —OR³, —NR³₂, —NR³₃+, —N(R³)C(O)R³, —O₂CR³, —CO₂R³, —C(O)NR³₂, straight or branched chain saturated alkyl group having from 1 to about 3 carbon atoms, and stright or branched chain unsaturated alkyl group having from 2 to about 3 carbon atoms, or two R¹'s on the same carbon atom are =O or =CR³₂; and each R³ is independently selected from the group consisting of —H, methyl and ethyl; or the pharmaceutically-acceptable salt thereof; and (B) a pharmaceutically-acceptable carrier.

27. The pharmaceutical composition of claim 26 wherein the anti-inflammatory compound has the structure:

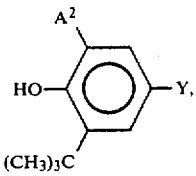

wherein A² is selected from the group consisting of unsubstituted C₁-C₃ saturated, straight-chain alkyl, unsubstituted C₂-C₆ unsaturated, straight-chain alkyl, and unsubstituted C₃-C₆ saturated or unsaturated branched-chain alkyl; each R¹ is independently selected from the group consisting of —H, —OH, methyl, and ethyl, or two R¹'s on the same carbon atom are =O or =CH₂; and wherein further no more than about two R¹ groups are a group other than —H; and each R³ is —H.

28. A method for treating diseases characterized by inflamation, said method comprising administering to a human or lower animal in need of such treatment a composition of claim 26.

29. A method for treating diseases characterized by inflammation, said method comprising administering to a human or lower animal in need of such treatment a composition of claim 27.

* * * * *